(12) United States Patent
Larsen et al.

(10) Patent No.: US 11,883,204 B2
(45) Date of Patent: Jan. 30, 2024

(54) ANALYTICAL TOILET WITH ACCESS PANEL

(71) Applicant: Medic, Inc., Provo, UT (US)

(72) Inventors: Joshua Larsen, Spanish Fork, UT (US); John W. Christiansen, American Fork, UT (US)

(73) Assignee: Hall Labs LLC, Provo, UT (US)

( * ) Notice: Subject to any disclaimer, the term of this patent is extended or adjusted under 35 U.S.C. 154(b) by 0 days.

(21) Appl. No.: 17/661,219

(22) Filed: Apr. 28, 2022

(65) Prior Publication Data

US 2022/0346719 A1    Nov. 3, 2022

Related U.S. Application Data

(60) Provisional application No. 63/181,095, filed on Apr. 28, 2021.

(51) Int. Cl.
| | |
|---|---|
| *A61B 5/00* | (2006.01) |
| *E03D 9/00* | (2006.01) |
| *A61B 10/00* | (2006.01) |
| *G01N 33/493* | (2006.01) |
| *E03D 11/13* | (2006.01) |

(52) U.S. Cl.
CPC .......... *A61B 5/6887* (2013.01); *A61B 10/007* (2013.01); *E03D 9/00* (2013.01); *E03D 11/13* (2013.01); *G01N 33/493* (2013.01)

(58) Field of Classification Search
None
See application file for complete search history.

(56) References Cited

U.S. PATENT DOCUMENTS

| | | | | |
|---|---|---|---|---|
| 5,097,539 | A * | 3/1992 | Tchorbadjian | E03D 9/08 4/443 |
| 8,984,676 | B2 * | 3/2015 | Zheng | E03D 9/052 4/219 |
| 10,738,454 | B2 * | 8/2020 | Spankowski | E03D 11/02 |
| 11,123,049 | B2 * | 9/2021 | Kramer | E03D 11/00 |
| 2014/0259351 | A1 * | 9/2014 | Spankowski | E03D 11/14 4/420 |
| 2018/0020984 | A1 * | 1/2018 | Hall | A47K 13/24 600/301 |
| 2018/0080923 | A1 * | 3/2018 | Hall | G01N 21/59 |
| 2019/0369085 | A1 * | 12/2019 | Tan | E03D 9/08 |
| 2022/0018105 | A1 * | 1/2022 | Mielke | E03D 9/002 |

* cited by examiner

*Primary Examiner* — Christine J Skubinna

(57) ABSTRACT

An analytical toilet is disclosed having at least one health and wellness sensor and a base supporting a bowl. A removable access panel is removably attached to the base. A space is provided between the base and the toilet, which is adapted to contain the at least one health and wellness sensor.

20 Claims, 5 Drawing Sheets

ANALYTICAL TOILET WITH ACCESS PANEL

CROSS-REFERENCE TO RELATED APPLICATIONS

This application claims the benefit under 35 U.S.C. § 119(e) of U.S. Provisional Patent Application No. 63/181,095 titled "Analytical Toilet with Removable Shroud" filed on 28 Apr. 2021, which disclosure is incorporated herein by reference in its entirety.

TECHNICAL FIELD

The present disclosure relates to analytical toilets. More particularly, it relates to analytical toilets equipped to provide health and wellness information to the user.

BACKGROUND

The ability to track an individual's health and wellness is currently limited due to the lack of available data related to personal health. Many diagnostic tools are based on examination and testing of excreta, but the high cost of frequent doctor's visits and/or scans make these options available only on a very limited and infrequent basis. Thus, they are not widely available to people interested in tracking their own personal wellbeing.

Toilets present a fertile environment for locating a variety of useful sensors to detect, analyze, and track trends for multiple health conditions. Locating sensors in such a location allows for passive observation and tracking on a regular basis of daily visits without the necessity of visiting a medical clinic for collection of samples and data. Monitoring trends over time of health conditions supports continual wellness monitoring and maintenance rather than waiting for symptoms to appear and become severe enough to motivate a person to seek care. At that point, preventative care may be eliminated as an option leaving only more intrusive and potentially less effective curative treatments. An ounce of prevention is worth a pound of cure.

Just a few examples of smart toilets and other bathroom devices can be seen in the following U.S. Patents and Published Applications: U.S. Pat. No. 9,867,513 entitled "Medical Toilet With User Authentication"; U.S. Pat. No. 10,123,784 entitled "In Situ Specimen Collection Receptacle In A Toilet And Being In Communication With A Spectral Analyzer"; U.S. Pat. No. 10,273,674 entitled "Toilet Bowl For Separating Fecal Matter And Urine For Collection And Analysis"; US 2016/0000378 entitled "Human Health Property Monitoring System"; US 2018/0020984 entitled "Method Of Monitoring Health While Using A Toilet"; US 2018/0055488 entitled "Toilet Volatile Organic Compound Analysis System For Urine"; US 2018/0078191 entitled "Medical Toilet For Collecting And Analyzing Multiple Metrics"; US 2018/0140284 entitled "Medical Toilet With User Customized Health Metric Validation System"; and US 2018/0165417 entitled "Bathroom Telemedicine Station." The disclosures of all these patents and applications are incorporated by reference in their entireties.

SUMMARY

In a first aspect, the disclosure provides an analytical toilet having at least one health and wellness sensor and a base supporting a bowl. A removable access panel is provided, which is removably attached to the base. A space between the base and the toilet is adapted to contain the at least one health and wellness sensor.

Further aspects and embodiments are provided in the foregoing drawings, detailed description, and claims.

BRIEF DESCRIPTION OF THE DRAWINGS

The following drawings are provided to illustrate certain embodiments described herein. The drawings are merely illustrative and are not intended to limit the scope of claimed inventions and are not intended to show every potential feature or embodiment of the claimed inventions. The drawings are not necessarily drawn to scale; in some instances, certain elements of the drawing may be enlarged with respect to other elements of the drawing for purposes of illustration.

DETAILED DESCRIPTION

Figure 1C:
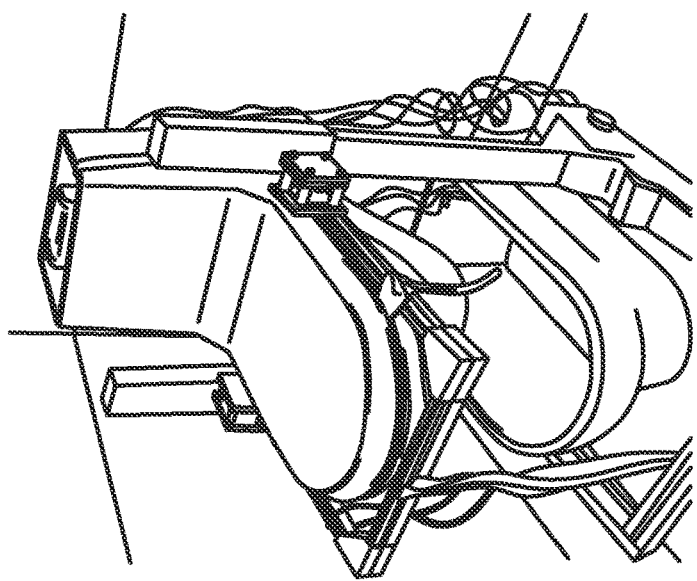
FIG. 1C is a perspective view of a typical prior art two-part toilet with the top lifted up with a specialized lifter.

The following description recites various aspects and embodiments of the inventions disclosed herein. No particular embodiment is intended to define the scope of the invention. Rather, the embodiments provide non-limiting examples of various compositions, and methods that are included within the scope of the claimed inventions. The description is to be read from the perspective of one of ordinary skill in the art. Therefore, information that is well known to the ordinarily skilled artisan is not necessarily included.

Definitions

The following terms and phrases have the meanings indicated below, unless otherwise provided herein. This disclosure may employ other terms and phrases not expressly defined herein. Such other terms and phrases shall have the meanings that they would possess within the context of this disclosure to those of ordinary skill in the art. In some instances, a term or phrase may be defined in the singular or plural. In such instances, it is understood that any term in the singular may include its plural counterpart and vice versa, unless expressly indicated to the contrary.

As used herein, the singular forms "a," "an," and "the" include plural referents unless the context clearly dictates otherwise. For example, reference to "a substituent" encompasses a single substituent as well as two or more substituents, and the like.

As used herein, "for example," "for instance," "such as," or "including" are meant to introduce examples that further clarify more general subject matter. Unless otherwise expressly indicated, such examples are provided only as an aid for understanding embodiments illustrated in the present disclosure and are not meant to be limiting in any fashion. Nor do these phrases indicate any kind of preference for the disclosed embodiment.

As used herein, "toilet" is meant to refer to any device or system for receiving human excreta, including urinals.

As used herein, the term "bowl" refers to the portion of a toilet that is designed to receive excreta.

As used herein, the term "base" refers to the portion of the toilet below and around the bowl supporting it.

As used herein, the term "user" refers to any individual who interacts with the toilet and deposits excreta therein.

As used herein, the term "excreta" refers to any substance released from the body including urine, feces, menstrual discharge, and anything contained or excreted therewith.

As used herein, the term "manifold" is intended to have a relatively broad meaning, referring to a device with multiple conduits and valves to controllably distribute fluids, namely water, liquid sample and air.

As used herein, the term "sensor" is meant to refer to any device for detecting and/or measuring a property of a person or substance regardless of how that property is detected or measured, including the absence of a target molecule or characteristic. Sensors may use a variety of technologies including, but not limited to, MOS (metal oxide semiconductor), CMOS (complementary metal oxide semiconductor), CCD (charge-coupled device), FET (field-effect transistors), nano-FET, MOSFET (metal oxide semiconductor field-effect transistors), spectrometers, volume measurement devices, weight sensors, temperature gauges, chromatographs, mass spectrometers, IR (infrared) detector, near IR detector, visible light detectors, and electrodes, microphones, load cells, pressure gauges, PPG (photoplethysmogram), thermometers (including IR and thermocouples), rheometers, durometers, pH detectors, scent detectors gas, and analyzers.

As used herein, the term "data connection" and similar terms are meant to refer to any wired or wireless means of transmitting analog or digital data and a data connection may refer to a connection within a toilet system or with devices outside the toilet.

As used herein, the prefix "nano-" is meant to refer to something in size such that units are often converted to the nano-scale for ease before a value is provided. For example, the dimensions of a molecule may be given in nanometers rather than in meters.

As used herein, "FET" is meant to refer to a field effect transistor, which is a device which uses an electric field to control the current flowing through a device. FETs are also known by the name "unipolar transistor".

Exemplary Embodiments

Figure 1B:
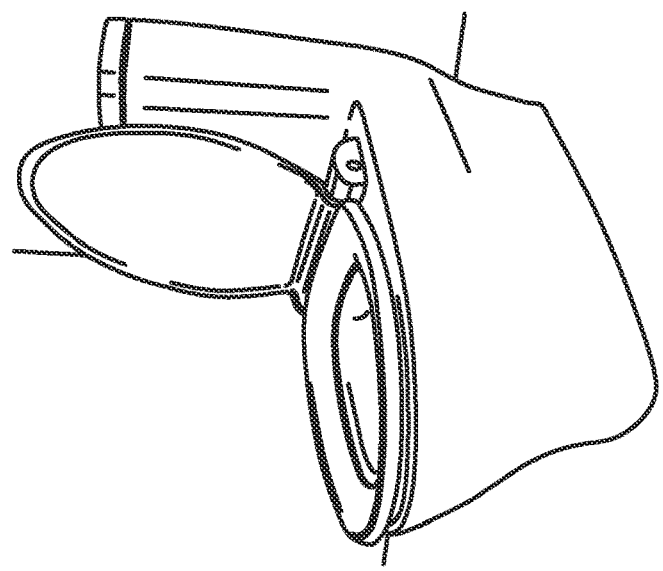
FIG. 1B is a perspective view of a typical prior art skirted toilet.
Figure 1A:
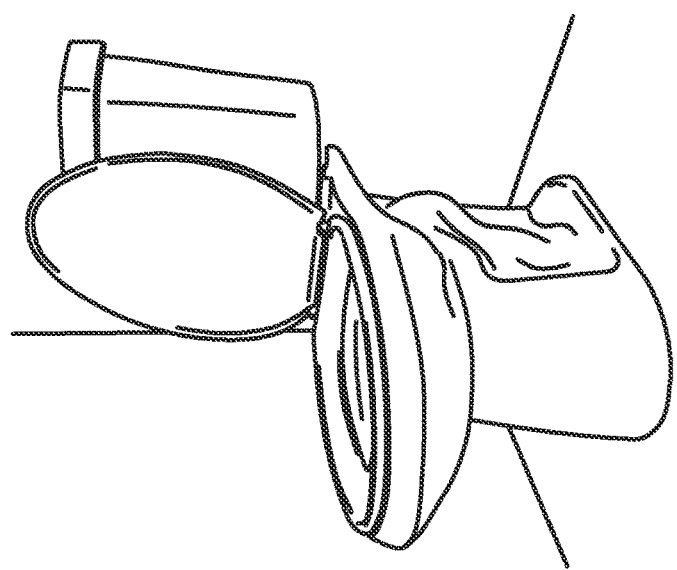
FIG. 1A is a perspective view of a typical prior art porcelain toilet.

The present disclosure relates to an analytical toilet with a variety of health and wellness sensors and/or modules for examining a user and their excreta. Conventional toilets do not provide space for the placement of additional hardware required for analytical, health and wellness toilets. Thus, it is necessary to change the external shape and/or internal configuration of its components. For example, the space around the relatively narrow base of a pedestal toilet, as shown in FIG. 1A, could be used. However, an external installation would be considered unsightly and leave delicate devices vulnerable to physical contact and damage. Placing a skirt around the base of the toilet, as shown in FIG. 1B, provides protection and a more visually appealing design but does not provide access to the interior for maintenance, repair, or replacement of equipment. A two-piece toilet with a removable top portion is shown in FIG. 1C. To gain access to the interior of the toilet, special equipment is needed to safely lift and accurately lower the top portion into place.

Figures 2A, 2B:
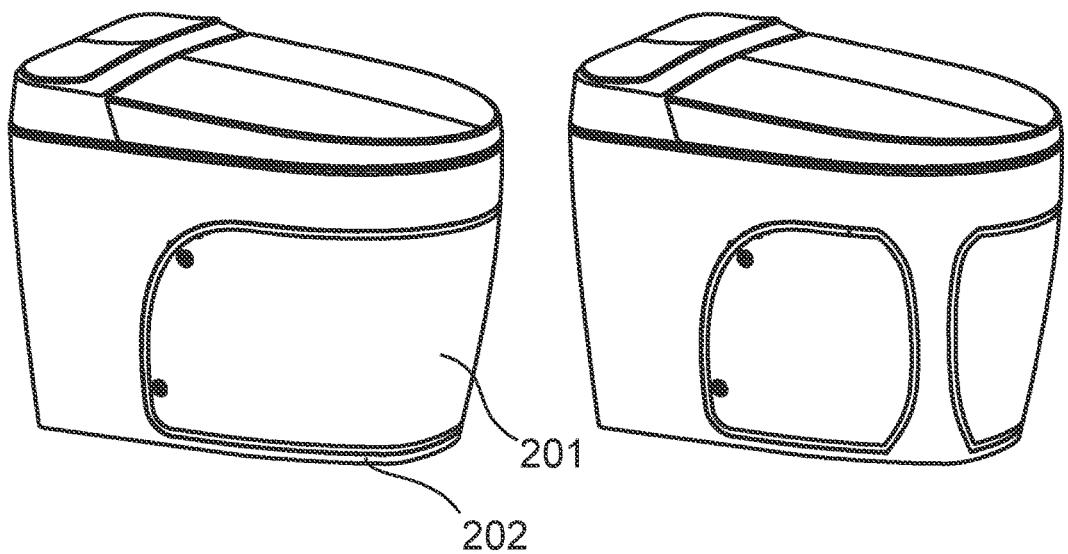
FIG. 2A is an isometric view of a first exemplary embodiment of an analytical toilet with a removeable access panel according to the present disclosure.
FIG. 2B is an isometric view of a second exemplary embodiment of an analytical toilet with removeable access panels according to the present disclosure.

Now referring to FIGS. 2A-B, the disclosed toilet 200 has one or more removeable access panel 201 around the front and sides of the toilet. This design provides for space around and beneath the bowl for additional components, wiring, and tubing. The external shape, size, and appearance of the toilet with the access panel installed is similar to that of a skirted toilet. The access panel 201 protects the additional hardware from damage (i.e., water, humidity, collision/contact) and provides a finished appearance for the product. The additional hardware (i.e., sensors, valves, manifold, electronics, controllers, processors, instrument panel, transducers, wireless and wired communication devices, etc.) can be assembled on and around the base 202 of the toilet 200. The access panel 201 is then installed to cover the additional hardware. The access panel can be removed for service or maintenance without the need for specialized lifting tools or the need to remove the toilet entirely from the base or floor mount. Removal of the access panel 201 does not affect toilet functionality.

The disclosed toilet may be installed in a bathroom using a simple floor mount identical to that used on the most basic pedestal toilets. Unlike skirted toilets, no special mounting hardware is required for installation. Further, the toilet is installable with a seal (e.g., caulk) around the base that is not disrupted by removing the access panel. The access panel does not provide structural support for the bowl or other toilet components. Therefore, the functionality of the toilet is not interrupted when the access panel is removed or even damaged.

The toilet base 202 can be constructed of ceramic, plastic, composite, or other materials, as may the bowl and other standard components. With the access panel removed, the toilet resembles a pedestal toilet in that it has space around the external surfaces of the toilet bowl and the flush path where hardware can be installed. The toilet base is designed with a flange having geometry to mate with the access panel. This flange may have a seal installed such that the seal between the toilet base and the access panel could be air, water, and/or dust tight. Accommodations are made on the toilet base for securing the access panel to the base. Depending on the method used for this connection, these accommodations could be simple cutouts in the base, or add-on components made of a different material from the primary base material to accept a particular fastener.

Figure 3:
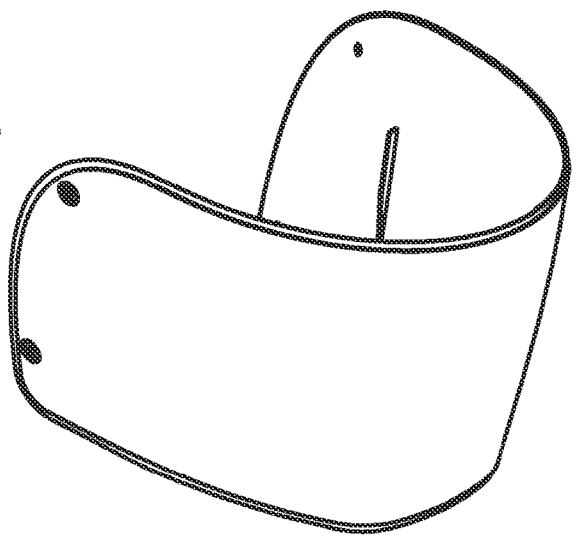
FIG. 3 is an isometric view of the access panel of the embodiment of FIG. 2A.

Now referring to FIG. 3, the removable access panel 201 can be constructed of plastic, composite, or other materials. The geometry of the access panel 201 is designed with draft such that the access panel 201 can be installed on the toilet in a general front-to-back direction. The access panel could be transparent, translucent, or opaque. The access panel 201 is designed with features to connect and secure the access panel to the base toilet. These features will vary based on the method used for this connection.

The removable access panel can be secured to the base using a variety of connection methods. The connection method is characterized by being secure during shipping, installation, and normal use, but still being removable for service or maintenance. The connection method could be designed for removal by anyone (i.e., requiring no specialized tools) or made more secure for removal only by service technicians (i.e., using a fastener style that requires a specialized tool for removal). Connection methods include, but are not limited to compliant clips, rotating cam locks, rotating clips, magnetic mounts, hook-and-loop fasteners, reusable adhesives, and threaded fasteners (e.g., screws or bolts). The advantages of this innovation include, but are not limited to, protecting the additional toilet hardware, providing acceptable product aesthetics, and allowing easy access for service and maintenance.

The access panel could be made transparent over part or all its surface to allow for observation of the functioning hardware. This observation could be purely based on curiosity, or it could allow a user to view physiological health indicators inside the toilet.

The access panel could be made translucent over part or all its surface to allow for indicator lights installed around the base toilet to provide lighting of various colors and brightness levels. This lighting could be used for decorative purposes or to provide an indication to the user related to the status of the product. In various exemplary embodiments, the access panel could be used as a screen to project images or text.

The access panel could be manufactured with various colors or surface finishes to allow for user selection of the toilet appearance at the time of purchase, or modification of the toilet appearance after purchase by replacing the access panel.

Beyond providing accessibility to the additional toilet hardware used for medical measurement, the access panel could permit accessibility for assembly or maintenance of "standard" toilet functions. This could include access to standard plumbing components, such as the flush system, or specialized health and wellness analysis components underneath the access panel.

Figure 4:
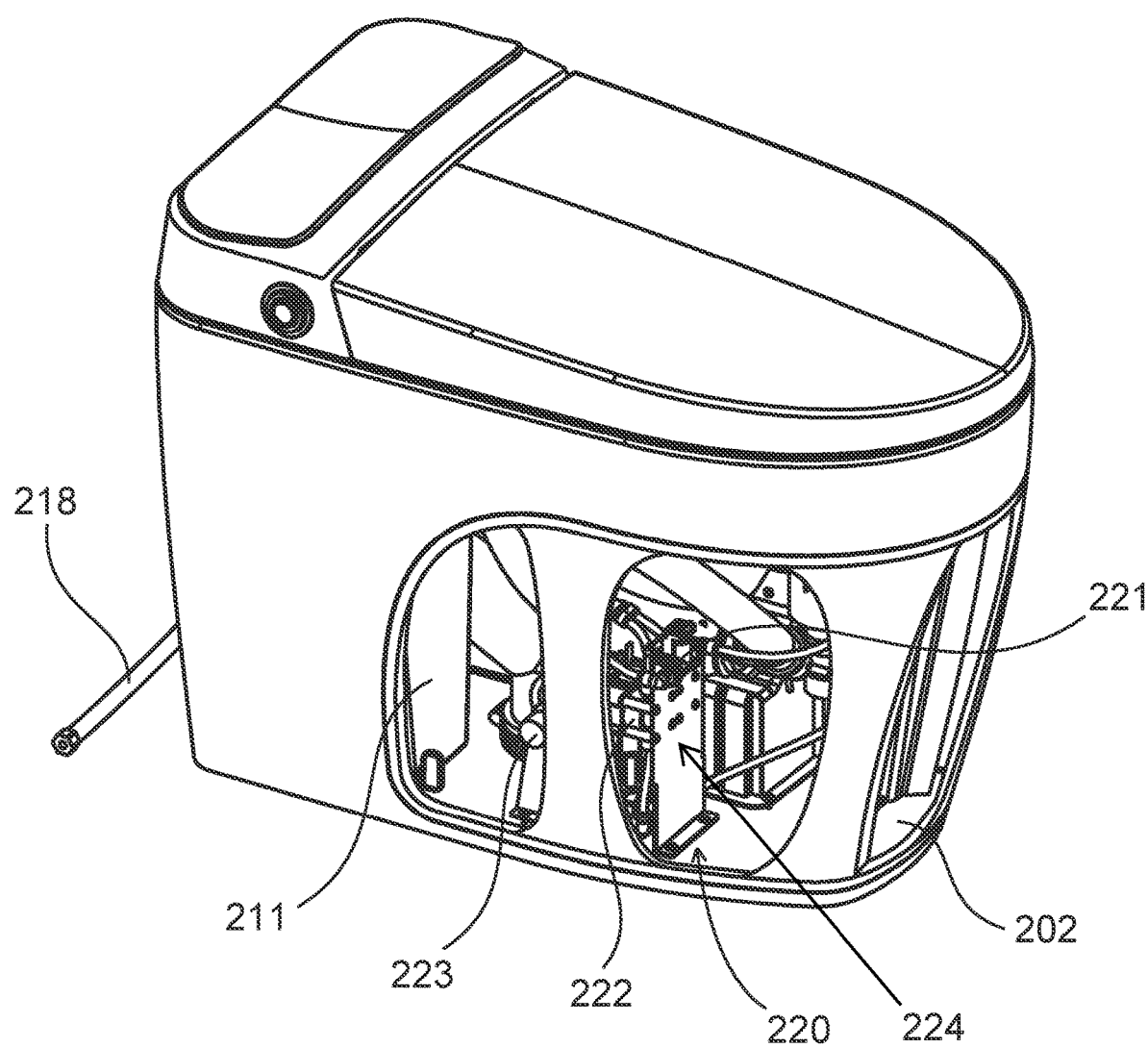
FIG. 4 is an isometric view of the right side of the analytical toilet of FIG. 2A with the access panel removed.
Figure 5:
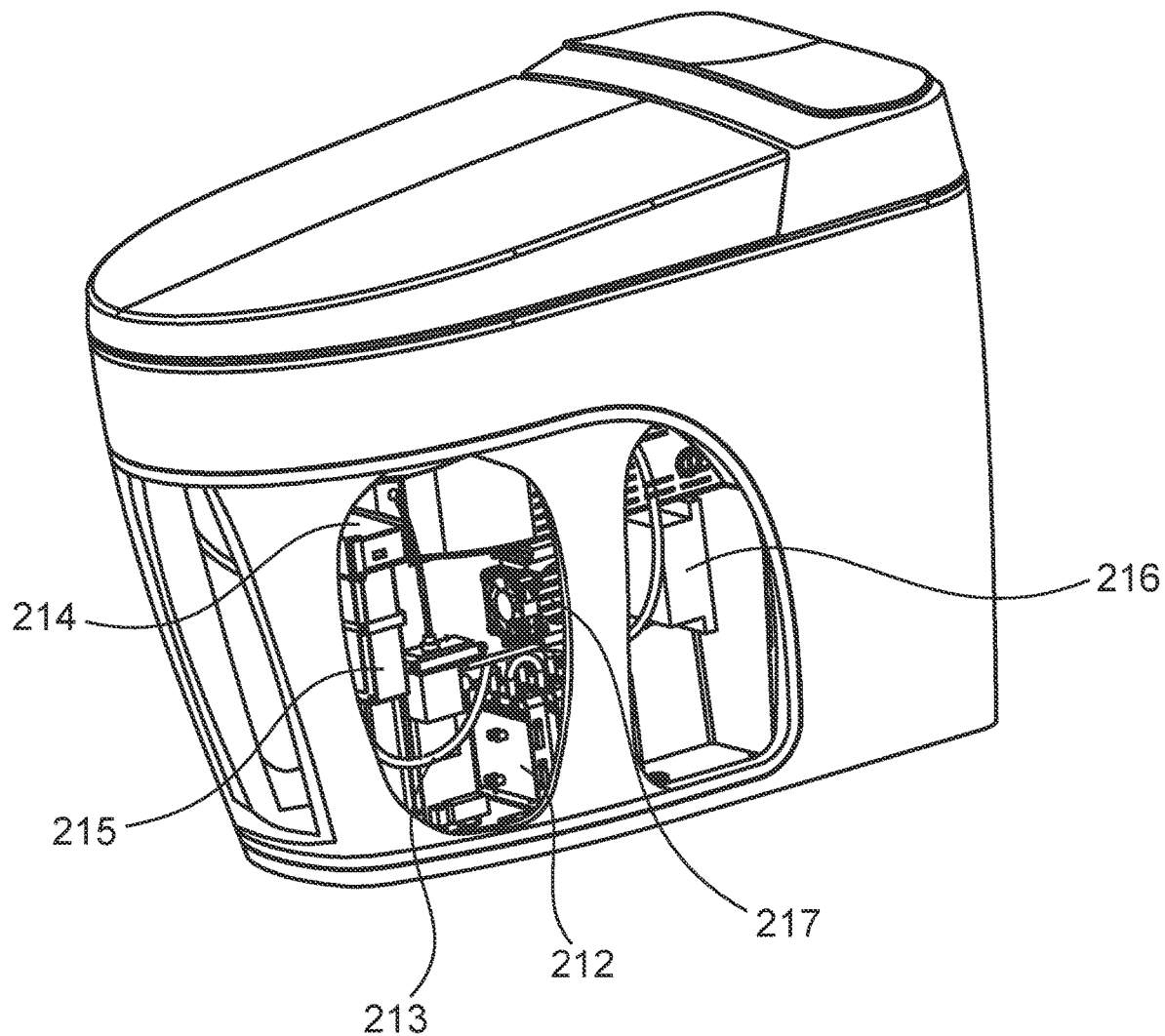
FIG. 5 is an isometric view of the left side of the analytical toilet of FIG. 2A with the access panel removed.

Now referring to FIGS. 4-5, the interior space behind the access panel 201 contains a variety of components related to the both the toilet's basic function and to its analytical function obtaining health and wellness data. In various exemplary embodiments, the interior of the toilet 200 includes a manifold system 224. The manifold 224 is responsible for the flow of samples, any other fluids needed for testing (e.g., reagents, dyes, dilutants), and cleaning the sensor. An analytical toilet with such a manifold is described in U.S. patent Ser. No. 16/812,019 entitled "Toilet with Digitally Controlled Manifold to Distribute Fluids" dated 6 Mar. 2020, the entire disclosure of which is included herein by reference.

In various exemplary embodiments, the interior of the toilet 200 contains, among other things, a flush tank 211, flush pump (not shown), one or more printed circuit boards 212 (PCB) with controllers and/or processors, a light source 213 (e.g., near infrared light) for a slit spectrometer 214, single board computer or minicomputer 215 providing processors and/or controllers for one or more components, power supplies 216 and 217, and uroflow measurement module 220. An exemplary uroflow module includes a bowl level sensor 221 in fluid communication with the bowl and a pressure regulator 222 and valve 223 controlling flow of water from the tank 211 or external water source 218 through the uroflow module into the bowl.

In various exemplary embodiments, the toilet contains one or more health and wellness sensors. These may be located in the bowl (completely or partially) or in the space around the bowl. In various exemplary embodiments, the excreta are tested for a variety of properties including volume, flow rate, color, weight, density, content, temperature, clarity, pH, settled gradient, and flow geometry. This may be done with a variety of sensors or testing methods including MOS, CCD, spectrometers, volume measurement devices, weight sensors, temperature gauges, chromatographs, mass spectrometers, pressure sensors, and gas analyzers. Additional sensors or tests may include electrocardiography, CCD, MOS/CMOS, spectrometers, chromatographs, FET, nanoFET, MOSFET, mass spectrometers, electrodes, microphones, load cells, pressure gauges, PPG, thermometers (including IR and thermocouples), rheometers, durometers, pH detectors, and scent detectors.

In various exemplary embodiments, the health and wellness detection/testing devices in the toilet system may be in the form of cartridges that are inserted into standardized interfaces. In such embodiments, the access panel preferably provides access to the interface for installation and replacement of testing cartridges. A toilet with a manifold and interchangeable test cartridges is described in U.S. patent Ser. No. 16/811,918 entitled "Toilet with Infrastructure for Analytical Devices" dated 6 Mar. 2020, the entire disclosure of which is included herein by reference.

Figure 6:
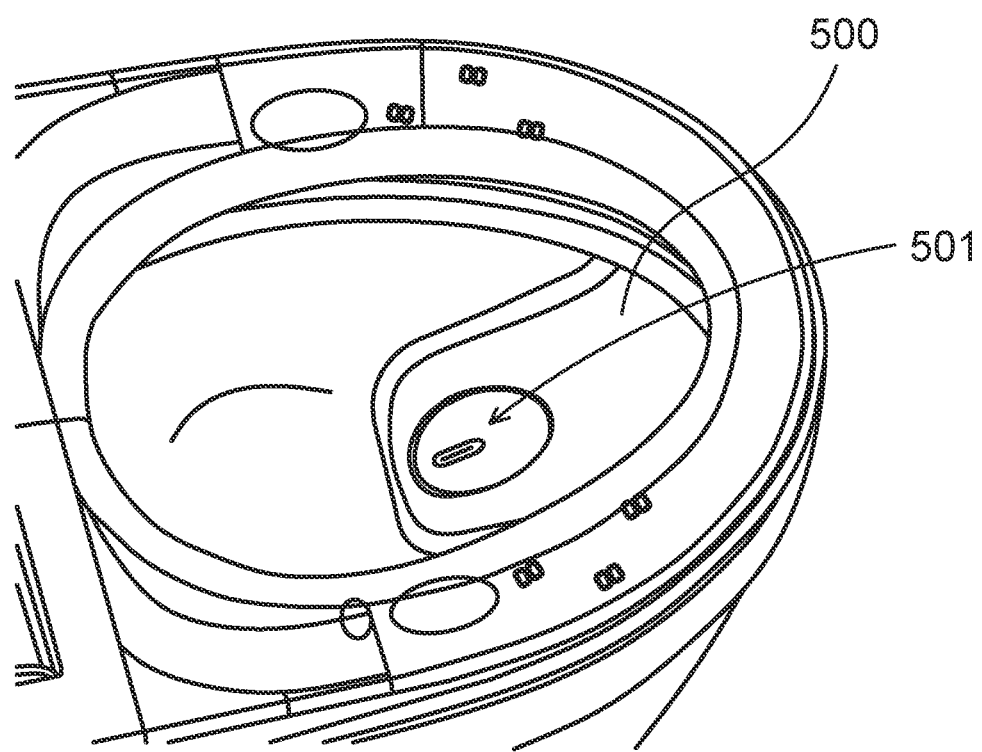
FIG. 6 is an isometric view of an exemplary embodiment of the analytical toilet's bowl according to the present disclosure.
Figure 7:
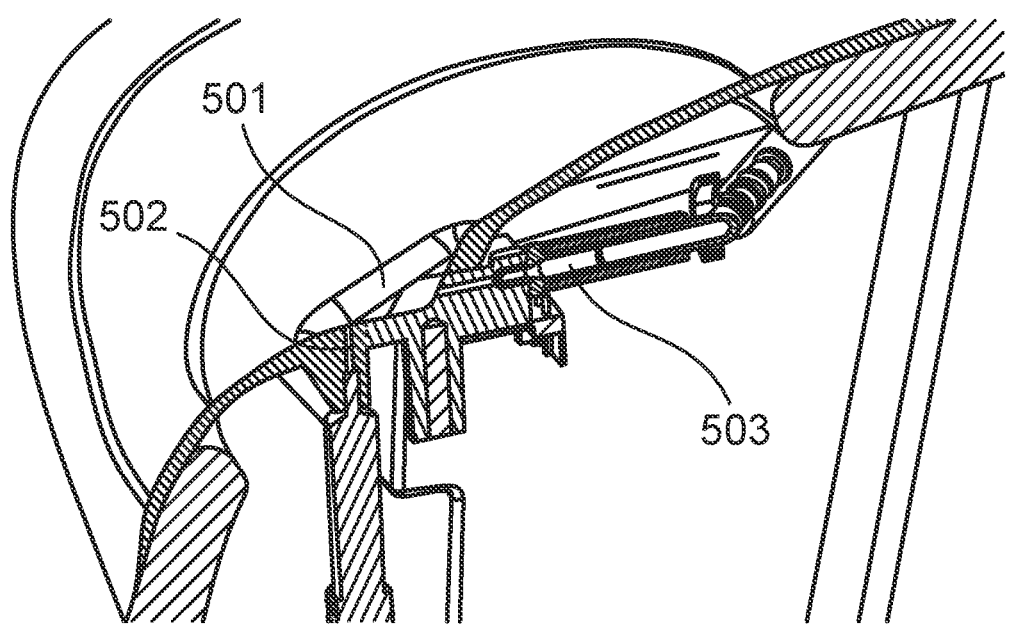
FIG. 7 is a side cross-sectional view of the bowl of FIG. 6.

Now referring to FIGS. 6-7, the interior of an exemplary embodiment of a toilet bowl 500 is shown. In various exemplary embodiments, the toilet bowl includes a urine collection slit 501 that is adapted to allow urine flowing down the side of the bowl to flow into a slit where it is retained at least temporarily. The light source 213 provides light to the slit. Light transmitted through the urine is examined with a spectrometer 214. A thermocouple 502 measures urine temperature, which is used to determine user body temperature. In such toilets, the flow of clean water through the mounting fixture to flush and/or refill the bowl passes through the slit 501 to rinse and clean it. An air conduit 503 provides air for drying the slit after rinsing.

An exemplary toilet with such a slit is disclosed in U.S. patent application Ser. No. 15/383,187 entitled "Capillary Slit Urine Sampling System" filed 19 Dec. 2016, the entire disclosure of which is referenced herein in its entirety. An exemplary toilet with a thermocouple system for determining body temperature based on urine temperature is disclosed in U.S. patent application Ser. No. 17/535,426 entitled "Thermally Isolated Temperature Sensor in a Toilet Bowl" dated 24 Nov. 2021, the entire disclosure of which is referenced herein in its entirety.

All patents, published patent applications, and other publications referred to herein are incorporated herein by reference. The invention has been described with reference to various specific and preferred embodiments and techniques. Nevertheless, it is understood that many variations and modifications may be made while remaining within the spirit and scope of the invention.

What is claimed is:

1. An analytical toilet, comprising:
   at least one health and wellness sensor;
   a base supporting a bowl;
   a removable access panel removably attached to the base; and
   a space between the base and the toilet adapted to contain the at least one health and wellness sensor;
   wherein the space containing the at least one health and wellness sensor is accessed by removing the access panel.

2. The analytical toilet of claim 1, wherein the at least one health and wellness sensor comprises at least one fecal sensor.

3. The analytical toilet of claim 2, wherein the at least one fecal sensor comprises at least one of CCD, MOS, CMOS, spectrometers, chromatographs, FET, nanoFET, MOSFET, mass spectrometers, electrodes, microphones, load cells, pressure gauges, PPG, thermometers, rheometers, durometers, pH detectors, and scent detectors.

4. The analytical toilet of claim 2, wherein the at least one fecal sensor detects at least one of weight, color, consistency, volume, density, content, temperature, pH, size and shape, excretion profile, sounds, and gas or fumes.

5. The analytical toilet of claim 1, wherein the at least one sensor comprises at least one urine sensor.

6. The analytical toilet of claim 5, wherein the at least one urine sensor comprises at least one of CCD, MOS, CMOS, spectrometers, chromatographs, FET, nanoFET, MOSFET, mass spectrometers, electrodes, microphones, load cells, pressure gauges, PPG, thermometers, rheometers, durometers, pH detectors, and scent detectors.

7. The analytical toilet of claim 5 wherein the at least one urine sensor detects at least one of volume, flow rate, color, weight, density, content, temperature, clarity, pH, settled gradient, and flow geometry.

8. The analytical toilet of claim 1, comprising at least one communication module.

9. The analytical toilet of claim 1, wherein the access panel comprises a polymer.

10. The analytical toilet of claim 1, wherein the access panel is attached to the base with one or more connectors chosen from the group consisting of compliant clips, rotating cam locks, rotating clips, magnetic mounts, and threaded fasteners.

11. The analytical toilet of claim 1, wherein the access panel comprises a generally U-shaped profile adapted to cover the front and sides of the base.

12. The analytical toilet of claim 1, wherein the access panel attaches to one side of the base.

13. The analytical toilet of claim 12, further comprising a second access panel removably attached to an other side of the base.

14. The analytical toilet of claim 1, wherein the access panel comprises a panel on a front of the toilet base.

15. The analytical toilet of claim 1, further comprising a manifold system adapted to provide fluid flow between the at least one health and wellness sensor and the bowl.

16. The analytical toilet of claim 1, further comprising a processor that controls the functions of the toilet system and processes data from the at least health and wellness sensor.

17. The analytical toilet of claim 1, wherein the bowl further comprises a urine collection slit adapted to detain urine at least temporarily.

18. The analytical toilet of claim 17, wherein the urine collection slit further comprises a spectrometer.

19. The analytical toilet of claim 17, wherein the urine collection slit further comprises a temperature sensor.

20. The analytical toilet of claim 17, further comprising an air conduit for drying the slit.

* * * * *